(12) United States Patent
Yu et al.

(10) Patent No.: US 7,264,969 B1
(45) Date of Patent: Sep. 4, 2007

(54) CARRIER SYSTEM FOR SPECIFIC ARTERY WALL GENE DELIVERY

(75) Inventors: Lei Yu, Carlsbad, CA (US); Sung Wan Kim, Salt Lake City, UT (US); Jae-Woon Nah, Suncheon (KR)

(73) Assignee: University of Utah Research Foundation, Salt Lake City, UT (US)

( * ) Notice: Subject to any disclaimer, the term of this patent is extended or adjusted under 35 U.S.C. 154(b) by 486 days.

(21) Appl. No.: 10/416,381

(22) PCT Filed: Nov. 9, 2001

(86) PCT No.: PCT/US01/47072

§ 371 (c)(1),
(2), (4) Date: May 9, 2003

(87) PCT Pub. No.: WO02/42426

PCT Pub. Date: May 30, 2002

Related U.S. Application Data

(60) Provisional application No. 60/247,320, filed on Nov. 10, 2000.

(51) Int. Cl.
*C12N 15/88* (2006.01)
*C12N 15/00* (2006.01)
*C12N 15/87* (2006.01)
(52) U.S. Cl. .................. 435/458; 435/455; 435/461
(58) Field of Classification Search .................. 514/10; 435/458, 455, 461
See application file for complete search history.

(56) References Cited

U.S. PATENT DOCUMENTS 5,462,990 A * 10/1995 Hubbell et al. ............ 525/54.1

FOREIGN PATENT DOCUMENTS

WO    WO9840502 /    * 9/1998

OTHER PUBLICATIONS (Haensler etal, Bioconjugate Chem, Polyamidoamine cascade polymers mediate efficient transfection of cells in culture, 4:372-379, 1993.*
Haensler et al, Bioconjugate Chem, 4: 372-379, 1993.*
Deonarain, 1998, Exp Opin Ther Patents, 8: 53-69, 1998.*
Zauner et al, Advanced Drug Delivery Reviews, 30:97-113, 1998.*
Romano et al, Stem Cells, 17: 191-202, 1999.*
Ogris et al, Gene Therapy, 6: 595-605, 1999.*
Dash et al, JBC, 275(6): 3793-3802, 2000.*
Ogris et al, Gene Therapy, 5: 1425-1433, 1998.*
Nah, Jae-Woon, et al. Artery Wall binding peptide-poly(ethylene glycol)-*grafted*-poly(L-lysine)-based gene delivery to artery wall cells. Journal of Controlled Release 78(273-284). 2002.

* cited by examiner

*Primary Examiner*—Deborah Crouch
*Assistant Examiner*—Magdalene Sgagias
(74) *Attorney, Agent, or Firm*—Clayton, Howarth & Cannon, P.C.

(57) ABSTRACT

An artery wall binding peptide (AWBP) based on the artery wall cell-binding domain of apolipoprotein B-100 was conjugated to a cationic backbone configured for forming a complex with a nucleic acid to produce a composition that enhances gene transfer to artery wall cells. An illustrative cationic backbone is poly(ethylene glycol)-grafted-poly(L-lysine) (PEG-g-PLL). Methods of making and using the composition for gene transfer are also described.

14 Claims, 7 Drawing Sheets

US 7,264,969 B1

CARRIER SYSTEM FOR SPECIFIC ARTERY WALL GENE DELIVERY

CROSS-REFERENCE TO RELATED APPLICATIONS

This application claims the benefit of U.S. Provisional Application No. 60/247,320, filed Nov. 10, 2000.

STATEMENT REGARDING FEDERALLY SPONSORED RESEARCH OR DEVELOPMENT

This invention was made with U.S. government support under Grant No. HL-65477 awarded by the National Institutes of Health. The U.S. government may have certain rights in the invention.

BACKGROUND OF THE INVENTION

This invention relates to gene delivery. More particularly, this invention relates to compositions of matter, methods of use thereof, and methods of making thereof for delivering genes.

Gene therapy provides significantly important opportunities for treating various kinds of life-threatening and gene-related disease by producing biologically active agents or stopping abnormal functions of the cells, such as genetic failure or uncontrollable proliferation of cells. Actual application of genes to human therapy is limited by several problems, including their instability in body fluids, non-specificity to the desired cells, degradation by nucleases, and low transfection efficiency. Gene delivery systems have been investigated in attempts to enhance gene expression and reduce cytotoxicity. S.-O. Han et al., Development of Biomaterials for Gene Therapy, 2 Mol. Ther. 302-317 (2000).

Among the various gene delivery systems, viral vectors, M. A. Rosenfield et al., Adenovirus-mediated Transfer of a Recombinant A1-antitrypsine Gene to the Lung Epithelium In Vivo, 252 Science 431-434 (1991); H. M. Temin, Safety Considerations in Somatic Gene Therapy of Human Disease with Retrovirus Vectors, 1 Hum. Gene Ther. 111-123 (1990), liposomal carriers, X. Gao & L. Huang, Cationic Liposome-mediated Gene Delivery, 2 Gene Ther. 710-722 (1995); A. R. Thierry et al., Systemic Gene Delivery: Biodistribution and Long-term Expression of a Transgene in Mice, 92 Proc. Nat'l Acad. Sci. USA 9742-9746 (1995); J. H. Senior et al., Interaction of Positively-charged Liposomes with Blood: Implications for Their Application In Vivo, 1070 Biochim. Biophys. Acta 173-179 (1991), and cationic polymers, Y.-B. Lim et al., Biodegradable Polyester, Poly [α-(4-aminobutyl)-L-glycolic acid], as a Non-toxic Gene Carrier, 17 Pharm. Res. 811-816 (2000); P. Lemieux et al., Block and Graft Copolymers and NanoGel Copolymer Networks for DNA Delivery into Cell, 8 J. Drug. Target. 91-105 (2000), S.-O. Han et al., Water Soluble Lipopolymer for Gene Delivery, 12 Bioconjug. Chem. 337-345 (2001), have been widely investigated in gene therapy areas. Although retroviruses, adenoviruses, and adeno-associated viruses have shown higher transfection efficiency in vitro, the application of viral vectors to the human body is also limited by safety problems such as the immune response against transfection systems, oncogenic effects, and the potential ability of endogenous virus recombination. These problems have stimulated the development of non-viral gene delivery. As non-viral vectors, liposomes and cationic polymers have been extensively investigated for a decade due to the advantages of safety and relatively low cost. Although higher transfection efficiency has been reported by liposomal gene carriers in vitro, A. R. Thierry et al., supra, some liposomal gene carriers are unstable in aqueous solution and aggregate in blood. J. H. Senior et al., supra. Cationic polymers including poly(L-lysine) ("PLL") and polyethyleneimine ("PEI") were able to condense plasmid DNA and protect it from enzymatic degradation, which resulted in enhancement of transfection efficiency. However, drawback, such as biocompatibility in the body, still remain before such polymers can be used for gene delivery. To overcome the biocompatibility problem, non-toxic biodegradable polymeric gene carriers have been developed as promising gene delivery materials. Y.-B. Lim et al., supra. However, the biodistribution of the polymer/pDNA complexes following the injection of complexes into the body is still unknown. For the enhanced delivery of genes to specific cells, polymeric gene carriers have been modified with specific cell targeting moieties such as galactose, M. Nishikawa et al., Hepatocyte-targeted In Vivo Gene Expression by Intravenous Injection of Plasmid DNA Complexed with Synthetic Multi-functional Gene Delivery System, 7 Gene Ther. 548-555 (2000), transferrin, E. Wagner et al., Influenza Virus Hemaglutinin HA-2 N-terminal Fusogenic Peptides Augment Gene Transfer by Transferrin-polylysine-DNA complexes: Toward a Synthetic Virus-like Gene-transfer Vehicle, 89 Proc. Nat'l Acad. Sci. USA 7934-7938 (1992), and antibody, W. Suh et al., Anti-JL1 Antibody Conjugated Poly(L-lysine) for Targeted Gene Delivery to Leukemia T Cells, 72 J. Control. Release 171-178 (2001).

Recently, a series of methoxy poly(ethylene glycol)-grafted-poly(L-lysine (PEG-g-PLL) gene carriers was synthesized for reducing cytotoxicity, increasing solubility in aqueous solution, and enhancing the transfection efficiency resulting from long-term expression compared to PLL in a human carcinoma cell line. Y. H. Choi et al., Polyethylene Glycol-grafted Poly-L-lysine as Polymeric Gene Carrier, 54 J. Control. Release 39-48 (1998). A lactose group was also coupled to the end of PEG-g-PLL for specific targeting to hepatoma cells. Y. H. Choi et al., Lactose-poly(ethylene glycol)-grafted Poly-L-lysine as Hepatoma Cell-targeted Gene Carrier, 9 Bioconjug. Chem. 708-718 (1998); Y. H. Choi et al., Characterization of a Targeted Gene Carrier, Lactose-Polyethylene Glycol-grafted Poly-L-lysine, and its Complex with Plasmid DNA, 10 Hum. Gene Ther. 2657-2665 (1999). Transfection efficiency of such Lac-PEG-g-PLL/pDNA complexes was increased several-fold higher than that of PLL/DNA complexes in Hep G2 cells. A7R5 and NIH 3T3 cell lines do not have lactose receptors on their surfaces; consequently, the transfection efficiency of Lac-PEG-g-PLL/pDNA complexes was much lower than in the Hep G2 cells.

It was well known that low-density lipoprotein (LDL) can be taken up by different types of cells (vascular endothelial cells, vascular smooth muscle cells, hepatocytes, and macrophages) via receptor-mediated endocytosis. In previous reports, J. S. Kim et al., In Vitro Gene Expression on Smooth Muscle Cells Using a Terplex Delivery System, 47 J. Control. Release 51-59 (1997); J. S. Kim et al., Terplex DNA Delivery System as a Gene Carrier, 15 Pharm. Res. 116-121 (1998), a terplex-DNA gene delivery system comprising plasmid DNA, low density lipoprotein (LDL), and hydrophobized poly(L-lysine) (H-PLL) enhanced gene transfer via the LDL receptor-mediated endocytosis pathway. The transfection efficiency of the terplex-DNA system was 2-5 times higher than that of Lipofectin™/pDNA in A7R5 murine smooth muscle cells. Lipofectin™ reagent is a 1:1 (w/w) liposome formulation of the cationic lipid N-[1-(2,3- dioleyloxy)propyl]-n,n,n-trimethylammonium chloride (DOTMA), and dioleoyl phosphotidylethanolamine (DOPE) in membrane filtered water. This system also showed significantly higher transfection efficiencies in vitro in artery wall cells, L. Yu et al., Terplex DNA Gene Carrier System Targeting Artery Wall Cells, 72 J. Control. Release 179-189 (2001), and in vivo in myocardium cells, D. G. Affleck et al., Augmentation of Myocardia Transfection Using Terplex DNA: a Novel Gene Delivery System, 8 Gene Ther. 349-353 (2001).

Gene delivery systems containing a specific cell-targeting moiety have the advantage in the efficient delivery to the desired cells or organs. Although PLL has been described as an efficient gene carrier, U. K. Laemmli, Characterization of DNA Condensates Induced by Poly(ethylene oxide) and Polylysine, 72 Proc. Nat'l Acad. Sci. USA 4288-4299 (1975), as an alternative to liposomes or viral vectors, PLL/pDNA complexes displayed some limitations such as the precipitation of PLL/pDNA complexes in high concentration and low biocompatibility in the human body. Y. H. Choi et al., 54 J. Control. Release 39-48 (1998), investigated PEGylated-PLL/pDNA complexes to overcome these limitations of PLL by conjugation of PEG to PLL. Although PEGylated-PLL was shown to be a biocompatible material in tissues, efficient transfection to specific cells still remained a problem to overcome.

In view of the foregoing, it will be appreciated that providing a composition for matter for specific gene delivery to artery wall cells would be a significant advancement in the art.

BRIEF SUMMARY OF THE INVENTION

An illustrative composition of matter according to the present invention comprises an artery wall binding peptide covalently coupled to a pharmaceutically acceptable cationic backbone, wherein the cationic backbone is configured for complexing with a nucleic acid. In illustrative embodiments of this invention, the artery wall binding peptide is SEQ ID NO:2 or a biologically functional equivalent thereof. In another illustrative embodiment of this invention, the artery wall binding peptide is present in a molar ratio to the cationic backbone of greater than 1:1. In still another illustrative embodiment of this invention, the artery wall binding peptide is present in a molar ratio to the cationic backbone of at least 2:1. The cationic backbone can comprise, for example, a cationic polymer, a cationic lipid, or a mixture thereof. Illustrative cationic polymers according the invention include poly(L-lysine), poly(ethyleneimine), polyamidoamine dendrimer, poly[α-(4-aminobutyl)-L-glycolic acid], chitosan, poly(2-dimethylamino)ethyl methacrylate, poly(ethylene glycol)-grafted-poly(L-lysine), and the like.

Another illustrative composition of matter according to the present invention has the formula:

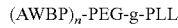

wherein AWBP is an artery wall binding peptide, n is an integer of at least 1, and PEG-g-PLL is poly(ethylene glycol-grafted-poly(L-lysine). In other illustrative embodiments of this invention n is about 4 and/or AWBP is SEQ ID NO:2.

Still another illustrative composition of matter according to the present invention comprises an artery wall binding peptide (SEQ ID NO:2) covalently coupled to poly(ethylene glycol)-grafted-poly(L-lysine). In another illustrative embodiments of this invention the artery wall binding peptide (SEQ ID NO:2) is covalently coupled to poly(ethylene glycol)-grafted-poly(L-lysine) in a molar ratio of about 4:1.

Yet another illustrative composition of matter according to the present invention comprises an artery wall binding peptide covalently coupled to poly(ethylene glycol)-grafted-poly(L-lysine). In other illustrative embodiments of this invention the artery wall binding peptide is covalently coupled to poly(ethylene glycol)-grafted-poly(L-lysine) in a molar ratio of about 4:1 and/or the artery wall binding peptide is SEQ ID NO:2.

An illustrative pharmaceutical composition according to the present invention comprises a mixture of:

(a) an effective amount of a composition comprising an artery wall binding peptide covalently coupled to a pharmaceutically acceptable cationic backbone, wherein the cationic backbone is configured for complexing with a nucleic acid; and (b) a pharmaceutically acceptable carrier.

Another illustrative pharmaceutical composition according to the present invention comprises a mixture of:

(a) an effective amount of a conjugate represented by the formula:

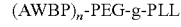

wherein AWBP is an artery wall binding peptide, n is an integer of at least 1, and PEG-g-PLL is poly(ethylene glycol)-grafted-poly(L-lysine); and (b) a pharmaceutically acceptable carrier.

Still another illustrative pharmaceutical composition according to the present invention comprises a mixture of:

(a) an effective amount of a composition comprising artery wall binding peptide covalently coupled to poly (ethylene glycol)-grafted-poly(L-lysine); and (b) a pharmaceutically acceptable carrier.

An illustrative method of making a composition having the formula:

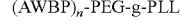

wherein AWBP is an artery wall binding peptide, n is an integer of at least 1, and PEG-g-PLL is poly(ethylene glycol)-grafted-poly(L-lysine), comprises:

(a) conjugating poly(ethylene glycol) to poly(L-lysine) to result in poly(ethylene glycol)-grafted-poly(L-lysine); and (b) conjugating artery wall binding peptide to the poly (ethylene glycol)-grafted-poly(L-lysine) to result in (AWBP)$_n$-PEG-g-PLL.

An illustrative method for delivering a nucleic acid to a cell bearing a receptor that binds an artery wall binding peptide comprises:

(a) mixing the nucleic acid with a composition of matter comprising an artery wall binding peptide covalently coupled to a cationic backbone, wherein the cationic backbone is configured for complexing with the nucleic acid, to form a complex;

(b) causing the complex to contact the cell such that the receptor binds the artery wall binding peptide, thereby delivering the nucleic acid to the cell.

Another illustrative embodiment of a method for delivering a nucleic acid to a cell bearing a receptor that binds an artery wall binding peptide comprises:

(a) mixing the nucleic acid with a composition of matter comprising an artery wall binding peptide covalently coupled to poly(ethylene glycol)-grafted-poly(L-lysine) to result in a complex comprising a nucleic acid portion, a poly(ethylene glycol)-grafted-poly(L-lysine) portion, and an artery wall binding peptide portion; and (b) causing the complex to contact the cell such that the receptor binds the artery wall binding peptide portion, thereby delivering the nucleic acid to the cell.

DETAILED DESCRIPTION

Figure 1:
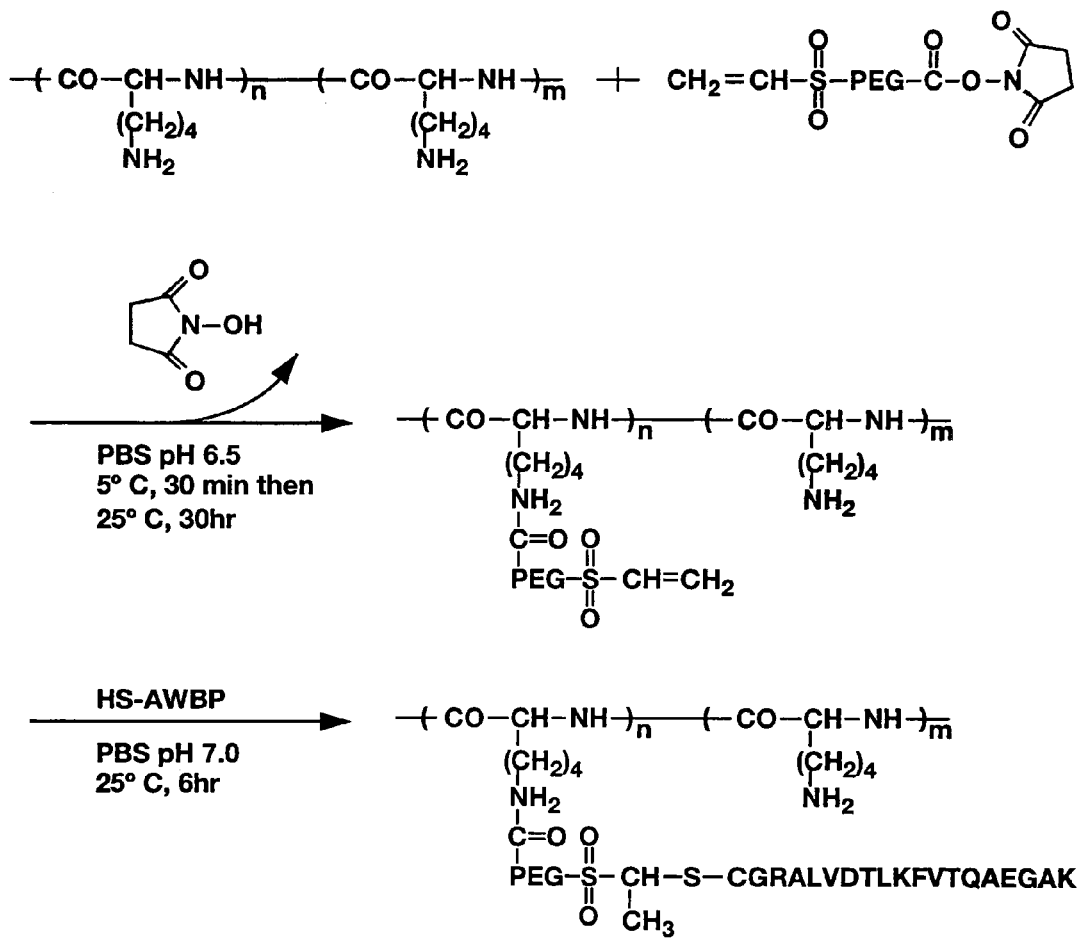
FIG. 1 shows an illustrative scheme for synthesis of AWBP-PEG-g-PLL comprising artery wall binding peptide (AWBP, SEQ ID NO:2 shown in single-letter code) conjugated to PEG-g-PLL.

Before the present carrier system for specific artery wall gene delivery is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a pharmaceutical composition comprising "a pharmaceutically acceptable carrier" includes a mixture of two or more of such carriers, reference to "an artery wall binding protein" includes reference to one or more of such artery wall binding proteins, and reference to "a plasmid" includes reference to a mixture of two or more of such plasmids.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "single-letter code" and similar terms refer to single-letter designations for the 20 amino acid residues found in peptides and proteins, as follows: A—alanine, C—cysteine, D—aspartic acid, E—glutamic acid, F—phenylalanine, G—glycine, H—histidine, I—isoleucine, K—lysine, L—leucine, M—methionine, N—asparagine, P—proline, Q—glutamine, R—arginine, S—serine, T—threonine, V—valine, W—tryptophan, and Y—tyrosine.

As used herein, "pDNA" means plasmid DNA.

As used herein, "cationic backbone" means a cationic molecule, complex, or conjugate, or the like, configured for forming a complex with a nucleic acid. Illustrative cationic backbones include cationic polymers and cationic lipids. Illustrative cationic polymers that can be used within the scope of the present invention include poly(L-lysine) (PLL), poly(ethyleneimine) (PEI), polyamidoamine dendrimer, poly[α-(4-aminobutyl)-L-glycolic acid] (PAGA), chitosan, poly(2-dimethylamino)ethyl methacrylate (pDMAEMA), PEG-g-PLL, and the like. An illustrative cationic lipid is N-[1-(2,3-dioleyloxy)propyl]-n,n,n-trimethylammonium chloride (DOTMA).

As used herein, "artery wall binding peptide" or "AWBP" mean a peptide configured for binding to a receptor that binds the artery wall cell-binding domain of apo B-100. According to the present invention, a ligand comprising such an artery wall binding peptide is coupled to a cationic backbone, such as PEG-g-PLL, so that upon endocytosis of the AWBP ligand any nucleic acid complexed to the cationic backbone moiety is also internalized by the cells.

Illustrative artery wall binding peptides include the peptide having the amino acid sequence identified as SEQ ID NO:2 and biologically functional equivalents thereof. Such functional equivalents retain functionality in binding the receptor and eliciting receptor-mediated endocytosis although they may be truncations, deletion variants, or substitution variants of SEQ ID NO:2 or include additional amino acid residues attached thereto.

As mentioned above, changes may be made in the structure of the artery wall binding peptide while maintaining the desirable receptor-binding characteristics. For example, certain amino acid residues may be substituted for other amino acid residues in a protein structure without appreciable loss of interactive binding capacity with structures such as, for example, antigen-binding regions of antibodies or binding sites of ligands such as an artery wall binding peptide. Since it is the interactive capacity and nature of a protein that defines that protein's biological functional activity, certain amino acid sequence substitutions can be made in a protein sequence and nevertheless obtain a protein with like properties. It is thus contemplated that various changes may be made in the sequence of an artery wall binding peptide without appreciable loss of its biological utility or activity.

Figure 2A:
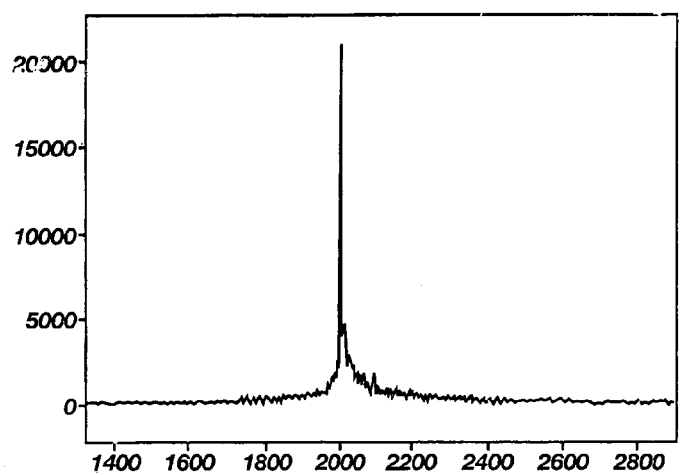
FIG. 2A shows the results of matrix-assisted laser desorption-time of flight (MALDI-TOF) mass spectrometry of AWBP.
Figure 2B:
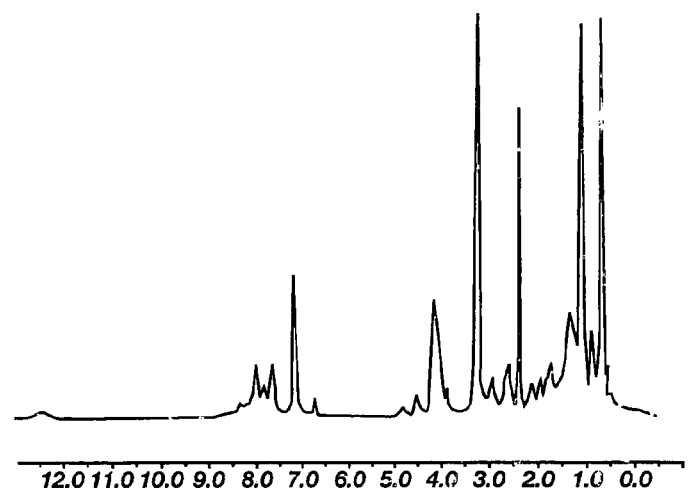
FIG. 2B shows a $^1$H-NMR spectrum of AWBP.
Figure 2C:
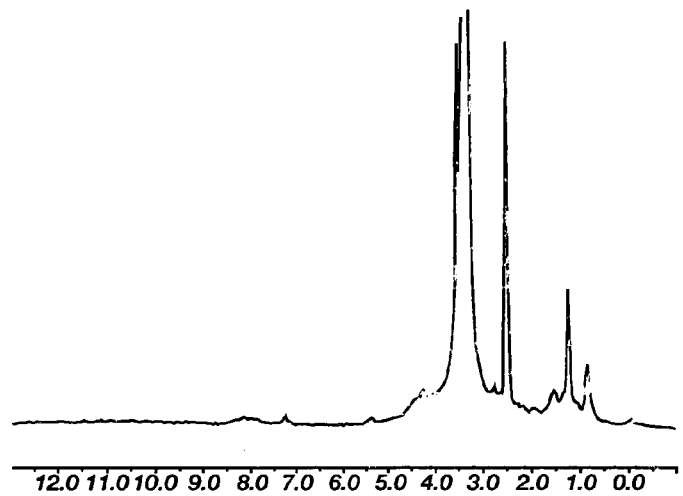
FIG. 2C shows a $^1$H-NMR spectrum of AWBP-PEG-g-PLL.

It is also well understood by the skilled artisan that inherent in the definition of a biologically functional equivalent protein or peptide is the concept that there is a limit to the number of changes that may be made within a defined portion of the molecule and still result in a molecule with an acceptable level of equivalent biological activity. It is also well understood that where certain residues are shown to be particularly important to the biological or structural properties of a protein or peptide, e.g. residues in active sites, such residues may not generally be exchanged.

Amino acid substitutions are generally based on the relative similarity of the amino acid side-chains relative to, for example, their hydrophobicity, hydrophilicity, charge, size, and the like. An analysis of the size, shape, and type of the amino acid side-chains reveals, for example, that arginine, lysine, and histidine are all positively charged residues; that alanine, glycine, and serine are all a similar size; and that phenylalanine, tryptophan, and tyrosine all have a generally similar shape. Therefore, based upon these considerations, the following conservative substitution groups or biologically functional equivalents have been defined: (a) Cys; (b) Phe, Trp, Tyr; (c) Gln, Glu, Asn, Asp; (d) His, Lys, Arg; (e) Ala, Gly, Pro, Ser, Thr; and (f) Met, Ile, Leu, Val. M. Dayhoff et al., Atlas of Protein Sequence and Structure (Nat'l Biomed. Res. Found., Washington, D.C., 1978).

To effect more quantitative changes, the hydropathic index of amino acids may be considered. Each amino acid has been assigned a hydropathic index on the basis of its hydrophobicity and charge characteristics, which are as follows: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. J. Kyte & R. Doolittle, A Simple Method for Displaying the Hydropathic Character of a Protein, 157 J. Mol. Biol. 105-132 (1982). It is known that certain amino acids may be substituted for other amino acids having a similar hydropathic index or score and still retain a similar biological activity. In making changes based on the hydropathic index, the substitution of amino acids whose hydropathic indices are within ±2 is preferred, within ±1 is particularly preferred, and within ±0.5 is even more particularly preferred.

It is also understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, within ±1 is particularly preferred, and within ±0.5 is even more particularly preferred.

Therefore, biologically functional equivalents of AWBP can be discovered without undue experimentation by a person of ordinary skill in the art according to the guidance and principles disclosed herein.

As used herein, a "pharmaceutically acceptable" component is one that is suitable for use with humans and/or animals without undue adverse side effects (such as toxicity, irritation, and allergic response) commensurate with a reasonable benefit/risk ratio. Illustratively, a "pharmaceutically acceptable" component includes one that is approved by a regulatory agency of the U.S. or other national government or a state government or listed in the U.S. Pharmacopeia or other generally recognized pharmacopeia for use in animals, and more particularly in humans.

The term "carrier" refers to a diluent, adjuvant, excipient, or vehicle with which the composition is administered. Such pharmaceutical carriers can be sterile liquids, such as water or aqueous saline solutions and aqueous dextrose and glycerol solutions.

As used herein, "effective amount" means an amount of a composition or pharmacologically active agent that is nontoxic but sufficient to provide the desired local or systemic effect and performance at a reasonable benefit/risk ratio attending any medical treatment.

As used herein, "administering" and similar terms mean delivering the composition to the individual being treated such that the composition is capable of being circulated systemically to the parts of the body where the AWBP portion of the composition can bind its receptor, e.g. artery walls. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

Apolipoprotein B-100 (apo B-100), a major protein component of LDL, contains many receptor-binding domains, such as LDL receptor-binding domain, artery wall cell-binding domain, and heparin-binding domain. It has been demonstrated that a synthetic peptide containing amino acid residues 1000-1016 of apo B-100 (Arg-Ala-Leu-Val-Asp-Thr-Leu-Lys-Phe-Val-Thr-Gln-Ala-Glu-Gly-Ala-Lys; SEQ ID NO:1) is the arterial binding domain of apo B-100. I. L. Shih et al., Focal Accumulation of an Apolipoprotein B-based Synthetic Oligopeptide in the Healing Rabbit Arterial Wall, 87 Proc. Nat'l Acad. Sci. USA 1436-1440 (1990). The focal accumulation of $^{125}$I-labeled apoB-based synthetic peptide at the healing edges of regenerating endothelial islands in balloon-catheter deendothelialized rabbit aorta suggested that this arterial wall-binding peptide could mediate accumulation of LDLs in arterial lesions. I. L. Shih et al., supra.

In the present invention, a synthetic peptide based on the arterial binding domain of apo B-100 was selected as a ligand for binding the compositions of the present invention to artery wall cells. A cysteine residue was added to the amino-terminus of the peptide to facilitate conjugation of the peptide to a cationic backbone. SEQ ID NO:2 shows the amino acid sequence of such a peptide.

In the present invention, a conjugate comprising AWBP covalently coupled to a cationic backbone was designed as a specific cell-targeting gene delivery system to artery wall cells. The artery wall is an attractive targeting tissue for gene therapy because it is distributed through all organs of the body. Although vascular gene transfer has been demonstrated with various techniques, a gene delivery system for arterial wall targeting has not previously been developed for the efficient treatment of cardiovascular diseases such as atherosclerosis and restenosis.

The gene delivery compositions of the present invention are made by covalently binding the artery wall binding peptide to the cationic backbone according to methods well known in the art. For example, amino groups on the peptide can react with acid chlorides of carboxylic acids to yield amide linkages or acid chlorides of sulfonic acids to yield sulfonamide linkages. By way of further example, amino groups can react with alkyl halides to yield alkylated amine linkages. Further, carboxylic acid groups on peptides can react with OH groups on a cationic backbone to form ester linkages, with amino groups to form amide linkages, and with SH groups to form thioester linkages. Still further, many crosslinking compounds are known in the art and are commercially available for crosslinking a peptide to, for example, a polymer or a lipid. Example 1 illustrates a vinylsulfone crosslinker for conjugating the SH group of cysteine to poly(ethylene glycol).

The compositions of the present invention are used by first mixing with a nucleic acid to be delivered to result in a complex. The positive charges on the composition interact with the negative charges on the nucleic acid to form the complex. The complex is then administered to the individual to be treated by gene therapy. The complex is prepared in a conventional form by mixture with a carrier, as described above. The mixture is then is administered to the individual by systemic administration, typically by subcutaneous, intramuscular, or intravenous administration, or intraperitoneal administration.

The size of the gene carrier and carrier/pDNA complex has been considered an important factor for enhancing the transfection efficiency since the particle size of the polymer/pDNA complex was reported to affect the transfection efficiency. J. Y. Cherng et al., Effect of Size and Serum Proteins on Transfection Efficiency of Poly((2-dimethylamino)ethyl methacrylate)-plasmid Nanoparticles, 13 Pharm. Res. 1038-1042 (1996). C. X. Song et al., Arterial Uptake of Biodegradable Nanoparticles for Intravascular Local Drug Delivery: Results with an Acute Dog Model, 54 J. Control. Release 201-211 (1998), reported a potentially useful particle size of about 70-160 nm for local intraluminal therapy of restenosis. Since drug carriers with a smaller particle size have resulted in higher arterial uptake compared to carriers with larger size, the size of the complexes was expected to be a dominating factor in the arterial wall lesions of the rapid blood flow which could wash out most of the drugs or therapeutic chemical agents from the arterial wall lesions within 20-30 minutes. Illustratively, the AWBP-PEG-g-PLL/pDNA complex according to the present invention has a size of about 100 nm (see Example 3), which is estimated as being an acceptable size for particles targeted for arterial wall lesions.

In gene expression studies designed to illustrate the operability and efficiency of compositions of the present invention (Example 4), transfection efficiencies of AWBP-PEG-g-PLL/pDNA complexes to bovine aorta endothelial cells and smooth muscle cells were 150-180 times higher than those of control carriers, PLL and PEG-g-PLL. In a transfection inhibition study (Example 4), luciferase activities of AWBP-PEG-g-PLL/pDNA complexes in both cells were significantly decreased with increase of free AWBP concentrations. However, the luciferase activities of control systems, such as PLL/pDNA complexes and PEG-g-PLL/pDNA complexes, were not significantly changed with the increase of free AWBP concentration. These results indicated that gene transfer of AWBP-PEG-g-PLL/pDNA complexes clearly proceeded by a receptor-mediated endocytosis pathway. Thus, it was clearly demonstrated that AWBP-PEG-g-PLL could function as a targeted gene delivery carrier to arterial wall cells via receptor-mediated endocytosis.

Progression of atherosclerotic lesions is marked by accumulation of altering layers of smooth muscle cells and endothelial cells. Therefore, the higher transfection efficiency of AWBP-PEG-g-PLL/pDNA complexes in these cells might be useful to evaluate the potential ability of to deliver a gene to the artery wall cells. The selective interactions between vascular endothelial cells and circulated complexes could be applied for a potential therapeutic approach. The rational design of the chemical structure of polymeric gene carriers such as AWBP-PEG-g-PLL with higher gene transfection efficiency and tissue specific gene delivery in vitro may become a very promising non-viral gene delivery system for cardiovascular gene therapy. Also, it is expected that the development of AWBP-PEG-g-PLL will be a turning point in the clinical therapy of artery related diseases such as athersclerosis and restenosis.

EXAMPLE 1

Synthesis of AWBP-PEG-g-PLL. Fifty milligrams of PLL hydrobromide (120 repeating units, $M_r$ 25,000, Sigma Chemical Co., St. Louis, Mo.) was dissolved in 1.0 ml of PBS (0.01 M $Na_2HPO_4$, 0.15 M NaCl, pH 6.5) and the solution was stirred for 40 min. at room temperature. Next, 27.2 mg of N-hydroxysuccinimide polyethylene glycol vinylsulfone (NHS-PEG-VS, $M_r$ 3400, Shearwater Polymers, Huntsville, Ala.) in 1.0 ml of dimethyl sulfoxide (DMSO, Aldrich, St. Louis, Mo.) was slowly added to the PLL solution and the reaction mixture was stirred for 3 hours at room temperature. After dialysis against distilled water in a dialysis tubing (Spectrum, Houston, Tex.) with a molecular weight cut-off of 15,000 for 1 day, the product was obtained by lyophilization to yield 60.0 mg of VS-PEG-g-PLL (77.6 wt. %).

Four milligrams of artery wall binding peptide (AWBP, $M_r$ 2008, SEQ ID NO:2; Genemed Synthesis, South San Francisco, Calif.) in 0.5 ml DMSO was added dropwise into a solution of 28.1 mg VS-PEG-g-PLL in 2.0 ml PBS (pH 7.0), and the reaction mixture was stirred for 6 hours at room temperature. The mixture was dialyzed for 4 days as described above and then lyophilized. The amount of final product was 20.0 mg of AWBP-PEG-g-PLL (62.2 wt. %). The final product was analyzed by 400 MHz $^1$H NMR (Varian, Palo Alto, Calif.) and then stored at −20° C. before use.

FIG. 1 illustrates the synthesis of a conjugate of artery wall binding peptide (AWBP; SEQ ID NO:2) to PEG-g-PLL, which conjugate is termed AWBP-PEG-g-PLL. The synthetic scheme comprises two reactions, first the synthesis of an activated PEG-g-PLL having a vinylsulfone group attached to the PEG portion of PEG-g-PLL, and then conjugation of AWBP to the vinylsulfone group to result in AWBP-PEG-g-PLL. Briefly, in the first step the N-hydroxysuccinimide (NHS) group of NHS-PEG-VS was conjugated to the amino group of PLL. The structure of the product and the conjugation reaction were analyzed by $^1$H-NMR as shown in FIGS. 2A-C. The content of PEG was estimated from the $^1$H-NMR analysis by the relative areas of alkyl groups in NHS-PEG-VS (—$CH_2CH_2$—, s, 3.21-3.77 ppm) and those of the side chains of PLL (—$CH_2CH_2CH_2$—, m, 1.05-1.90 ppm). In a second reaction, AWBP was conjugated to the end of the vinylsulfone group of VS-PEG-g-PLL. $^1$H-NMR analysis determined that 4 mol of AWBP were reacted with one mole of VS-PEG-g-PLL by the comparison of peaks at 7.3 ppm (aromatic group from phenylalanine) and 0.5-1.5 ppm (lysine peak from PLL). In addition, the specific proton peak (11.85-12.61 ppm) (FIG. 2B) of the thiol group on AWBP totally disappeared in the spectra obtained of AWBP-PEG-g-PLL (arrow in FIG. 2C), which indicated that the thiol groups of the peptide were completely conjugated to the vinylsulfone group of VS-PEG-g-PLL.

EXAMPLE 2

Gel band shift and DNase protection assay. A plasmid encoding firefly luciferase driven by the cytomegalovirus (CMV) promoter was constructed by inserting the luciferase gene into the mammalian gene expression plasmid pMNK at the MluI and KpnI restriction sites (Promega, Madison, Wis.). The plasmid DNA was transformed into *Escherichia coli* DH5α and amplified in terrific broth at 37° C. overnight with vigorous shaking at 225 rpm. The amplified plasmid DNA was purified using a Qiagen Maxi plasmid purification kit. The purity and concentration of the obtained plasmid DNA in Tris-EDTA (TE) buffer were determined by ultraviolet (UV) absorbance at 260 nm. The optical density ratios at 260 to 280 nm of the plasmid DNA were in the range of 1.7-1.8. The absence of gene rearrangement during cloning and propagation of the plasmid DNA was confirmed by restriction digest using SalI and EcoRI (Boehringer Mannheim GmbH, Germany) and 1% agarose gel electrophoresis.

AWBP-PEG-g-PLL/pDNA complexes were prepared at various charge ratios ranging from 0.1/1 to 20/1 (+/−) in HEPES-buffered saline (15 mM HEPES, 150 mM NaCl, pH 7.3) (HBS) and incubated for 20 minutes at room temperature. Afterwards, the samples were fractionated by electrophoresis through a 0.8% agarose gel at 100 V for 40 minutes and stained with ethidium bromide (0.5 µg/ml) for 45 minutes. DNA was then visualized with a UV illuminator.

AWBP-PEG-g-PLL/pDNA complexes were prepared at the charge ratios of 2/1 (+/−) and incubated in the presence of 10 times excess of DNase I. At 0, 5, 10, 15, 20, 60, and 120 minutes after incubation, 50 µl of the sample was transferred into another tube and mixed with 100 µl of stop solution (400 mM NaCl and 100 mM EDTA) using mild agitation with a vortexer. The sample was then mixed with 12 µl of 10% (w/v) sodium dodecyl sulfate (SDS) and incubated at 65° C. overnight. DNA was extracted with the mixture of Tris-EDTA saturated phenol:chloroform:isoamyl alcohol (25:24:1, v/v). The extracted DNA was precipitated with 700 µl of absolute ethanol at 12,000 rpm for 30 minutes and washed with 70% ethanol. The DNA precipitate was air-dried and then dissolved in 10 µl TE buffer. The plasmid integrity was assessed by electrophoresis in a 1% agarose gel.

Figure 3A:
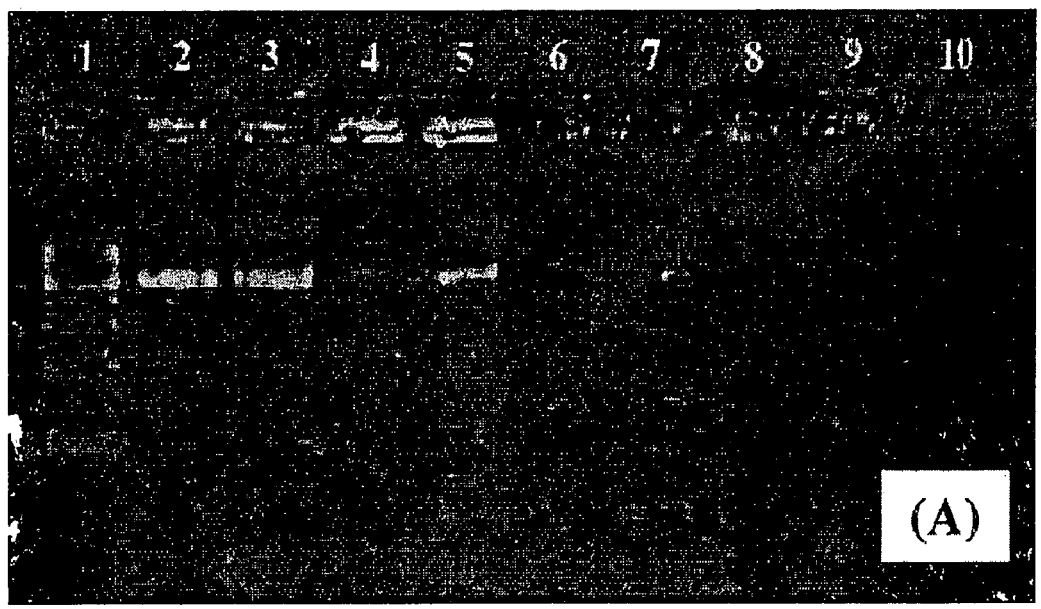
FIG. 3A shows a gel band shift assay of AWBP-PEG-g-PLL/pDNA complexes: lane 1, 300 ng of 1 kbp DNA step ladder molecular mass marker; lane 2, 360 ng of plasmid DNA; lanes 3-10, charge ratio of polymer/plasmid DNA=0.1, 0.2, 0.5, 1, 2, 3, 5, and 10, respectively.

Formation of AWBP-PEG-g-PLL/pDNA complexes between negatively charged plasmid DNA and positively charged AWBP-PEG-g-PLL was observed by gel band shift assay as shown in FIG. 3A. When a fixed amount of pCMV-Luc was titrated with AWBP-PEG-g-PLL, the electrophoretic mobility of DNA was retarded with increasing amount of AWBP-PEG-g-PLL. The complexes of pDNA and AWBP-PEG-g-PLL in lanes 6-10 showed weaker band in fluorescence intensity due to the exclusion of ethidium bromide after the formation of complexes. Complete complex formation was achieved at and above 1/1 (+/−) charge ratio of DNA (FIG. 3A, lanes 6-10).

Figure 3B:
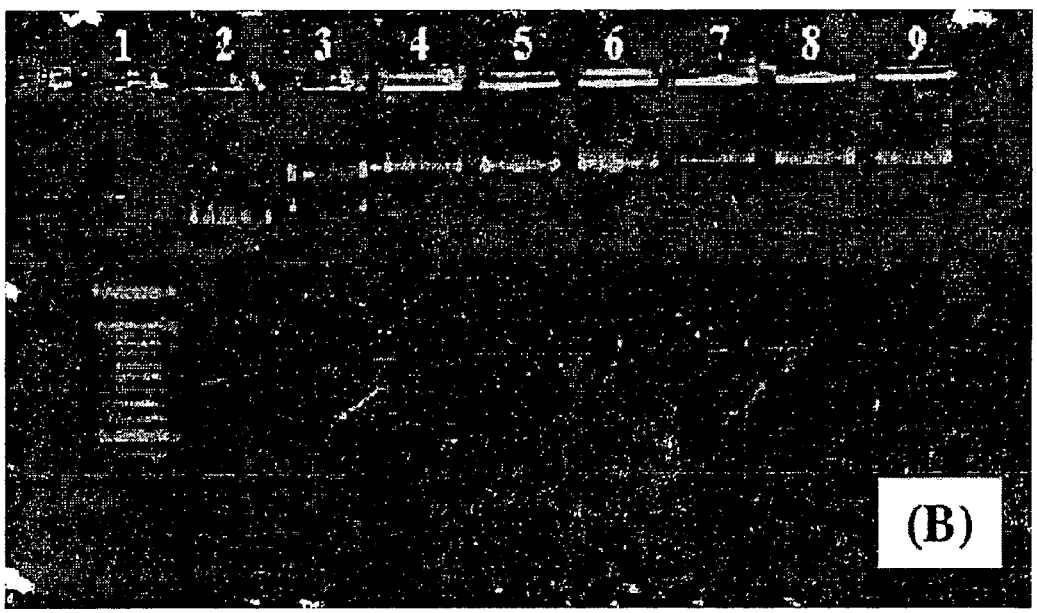
FIG. 3B shows a DNase protection assay of AWBP-PEG-g-PLL/pDNA complexes: lane 1, 100 bp DNA step ladder; lane 2, plasmid DNA; lanes 3-9, incubation times of 0, 5, 10, 15, 30, 60, 120 minutes, respectively.

AWBP-PEG-g-PLL could protect pDNA from digestion with DNase for at least 2 hours at 37° C. (FIG. 3B), whereas naked DNA was completely digested by DNASE within 5 to 10 minutes of incubation at 37° C. (data not shown).

EXAMPLE 3

Particle size and morphology. The particle size of AWBP-PEG-g-PLL/pDNA complexes was measured by zeta potentiometer. AWBP-PEG-g-PLL/pDNA complexes were prepared as described above and diluted 4 times in the cuvette. The sample was subjected to mean particle size measurement by Malvern Zeta-Sizer 3000 (Malvern Instruments, U.K.) at 25° C., pH 7.0, and 677 nm wavelength with constant angle of 15°.

The morphology of AWBP-PEG-g-PLL/pDNA complexes was confirmed by atomic force microscopy (AFM). Twenty microliters of AWBP-PEG-g-PLL/pDNA complexes (0.1 mg/ml) in PBS was placed on a $MgAc_2$ treated mica, A. Maheshwari et al., Soluble Biodegradable Polymer-based Cytokine Gene Delivery for Cancer Treatment, 2 Mol. Ther. 121-130 (2000), surface. The mica surface was rinsed gently with deionized water and dried with nitrogen gas. AFM images were obtained by Nanoscope II SFM (Digital Instruments, Santa Barbara, Calif.) at room temperature with cantilever oscillation frequencies between 12 and 24 kHz.

Figure 4:
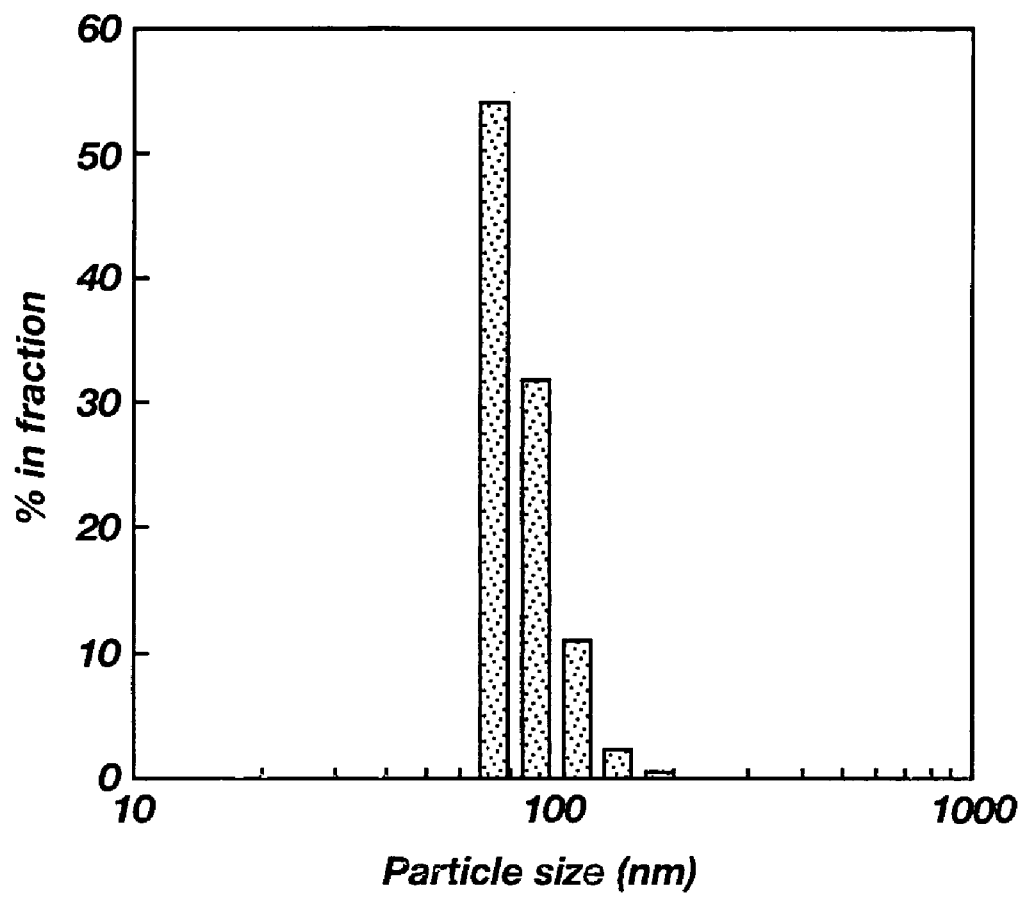
FIG. 4 shows particle size distributions of AWBP-PEG-g-PLL/pDNA complexes measured by zeta potentiometer.
Figure 5:
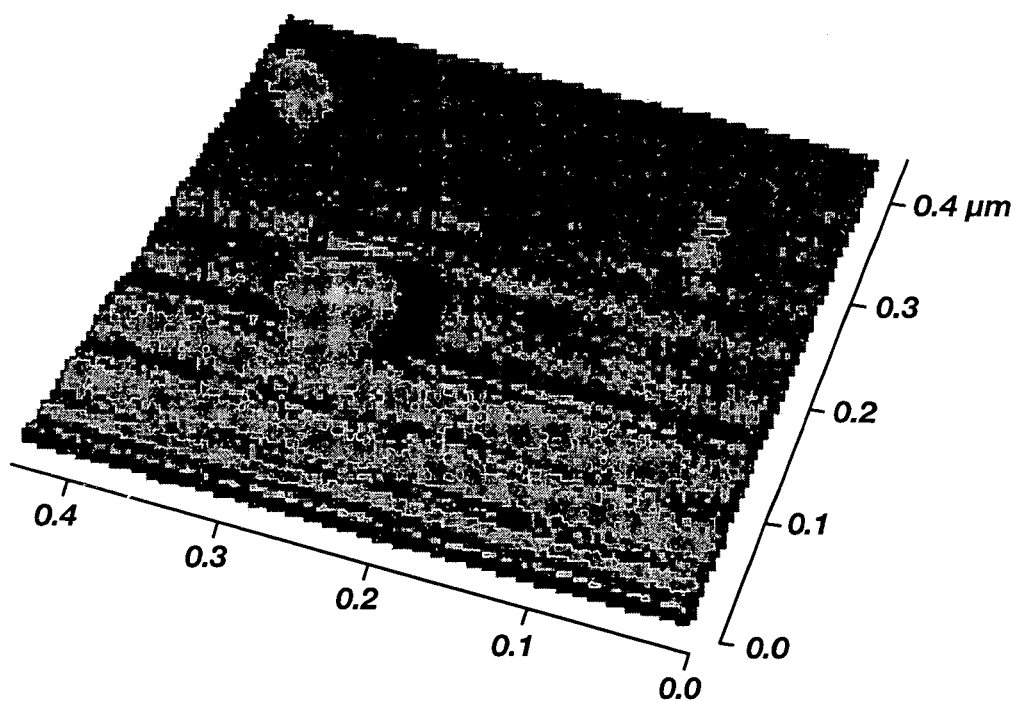
FIG. 5 shows surface morphology of an AWBP-PEG-g-PLL/pDNA complex (2/1, +/−) measured by atomic force microscopy (AFM).

The particle size of AWBP-PEG-g-PLL/pDNA was estimated as 85.9±5.3 nm with relatively narrow and unimodal size distributions ranging from 70.8 to 112.2 nm (FIG. 4) by zeta potentiometer. The morphology of AWBP-PEG-g-PLL/pDNA complex was determined to be spherical shapes with a diameter around 100 nm by atomic force microscopy (AFM) (FIG. 5), these data were in agreement with the results from the zeta potentiometer. This suggests that AWBP-PEG-g-PLL/pDNA complexes possess an acceptable size to enter the endosome of cells.

EXAMPLE 4

Gene expression. (Transfection assay) Primary bovine aorta endothelial cells and smooth muscle cells were prepared, cultured, characterized, and identified as described in L. Yu et al., supra. Bovine aorta endothelial cells ($5 \times 10^5$/well) and smooth muscle cells ($2 \times 10^5$/well) were seeded in 24-well plates with 1 ml Dulbecco's modified Eagle medium (DMEM, Hyclone Laboratories, Logan, Utah) containing 10% fetal bovine serum (FBS, Hyclone Laboratories) and incubated for 24 hours to 70-80% confluency. The AWBP-PEG-g-PLL/pCMV-Luc complexes were freshly prepared in PBS for the transfection with fixed amount of plasmid DNA (2 μg/well) and various amounts of AWBP-PEG-g-PLL. After incubation of complexes for 30 minutes at room temperature, 100 μl of complex solution was added to the cells and then incubated for 3 hours at 37° C. in 5% $CO_2$ atmosphere. After replacement of media, the cells were incubated for 40 hours under the same conditions. The cells were washed three times with PBS buffer and made ready for the reporter gene expression assay.

(Transfectioninhibition assay). Bovine aorta endothelial cells ($5 \times 10^5$/well) and smooth muscle cells ($2 \times 10^5$/well) were seeded in 24-well plates 1 day prior to transfection with 70 to 80% confluence. The AWBP-PEG-g-PLL/pCMV-Luc complexes were freshly prepared in PBS buffer for the transfection with a fixed amount of plasmid DNA (2 μg/well) and AWBP-PEG-g-PLL (4 μg/well). After addition of various amounts of free artery wall binding peptide (range from 31.3 μM to 1.0 mM) for 20 minutes at 4° C., 100 μl AWBP-PEG-g-PLL/pCMV-Luc solution was added to the cells. All the other conditions were the same as described above for the transfection assay.

(Gene expression assay) Transgene expression was evaluated by luciferase activity of cell lysates from transfected bovine aorta endothelial cells and smooth muscle cells. Measurement of luciferase activity was performed according to the manufacturer's instruction (Luciferase Assay System, Promega, Madison, Wis.). Briefly, the transfected cells were lysed with 1x lysis buffer (1% Triton X-100), 100 mM $KPO_4$, 2 mM dithiothreitol, 10% glycerol, and 2 mM EDTA, pH 7.8) for 15 minutes at room temperature. To measure the luciferase activity, 20 μl aliquot of cell lysate was mixed with 50 μl of luciferase assay reagent at room temperature and inserted in the luminometer. Light emission was measured in triplicate over 10 s and expressed as relative light units (RLUs). RLUs were normalized from the protein content of each sample, which was determined by BCA protein assay.

Figure 6A:
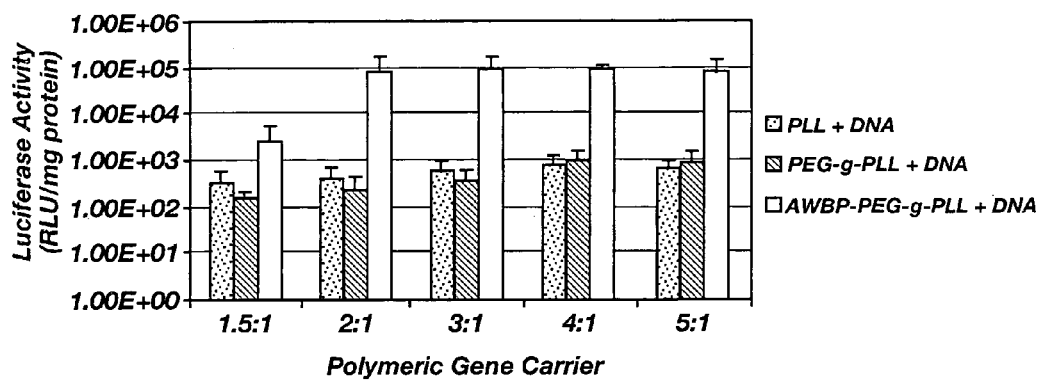
FIGS. 6A and 6B show AWBP-PEG-g-PLL mediated gene transfer (open bars) to bovine aorta endothelial cells (A) and smooth muscle cells (B); PLL (shaded bars) and PEG-g-PLL (dark bars) were used as negative control gene carriers.
Figure 6B:
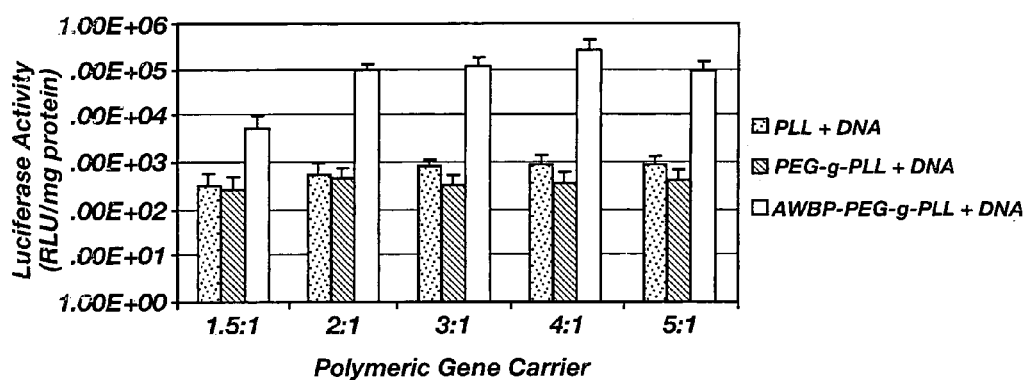

The transfection efficiencies of AWBP-PEG-g-PLL/pCMV-Luc complexes to artery wall cells were analyzed by in vitro transfection assay and in vitro transfection inhibition assay. Luciferase activities of cell lysate from both bovine aorta endothelial cells (FIG. 6A) and smooth muscle cells (FIG. 6B) transfected with AWBP-PEG-g-PLL were significantly increased with the ratio of AWBP-PEG-g-PLL to plasmid DNA from 1.5:1 to 2:1, but remained constant with further increasing the ratio from 2:1 to 5:1. This result indicated that AWBP-PEG-g-PLL/pDNA complexes were taken up by the artery wall cells underwent a receptor-mediated endocytosis pathway. The transfection efficiencies of AWBP-PEG-g-PLL/pDNA complexes were 150-180 times higher than those of control systems such as PLL/pDNA and PEG-g-PLL/pDNA, regardless of employed charge ratios. These results indicate that incorporation of AWBP to the PEG-g-PLL backbone was significantly enhanced the gene transfer to artery cell walls.

Figure 7A:
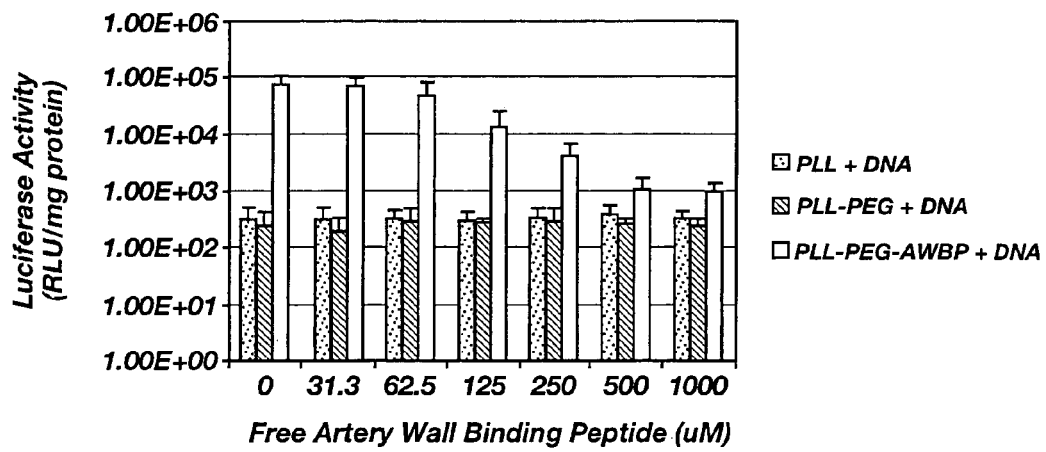
FIGS. 7A and 7B show inhibition of AWBP-PEG-g-PLL mediated gene transfer (open bars) to bovine aorta endothelial cells (A) and smooth muscle cells (B) with free AWBP; PLL (shaded bars) and PEG-g-PLL (dark bars) were used as negative control gene carriers.
Figure 7B:
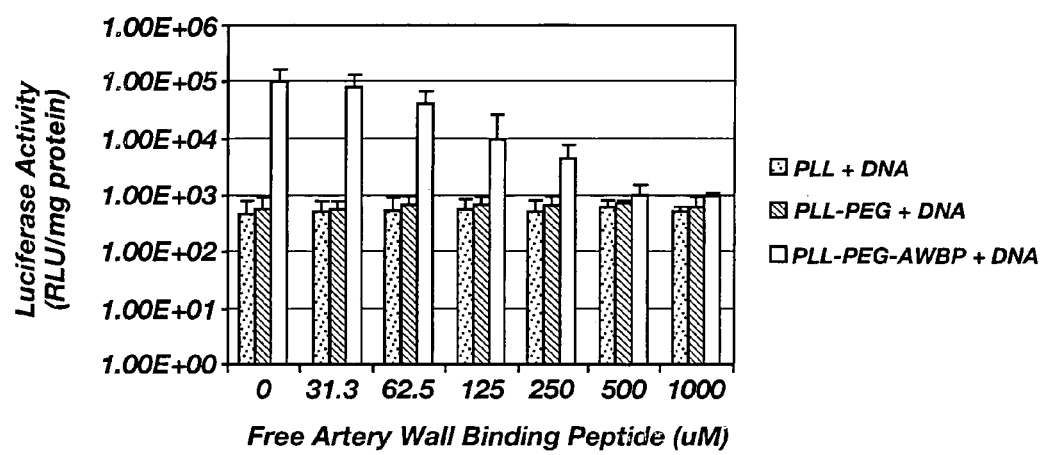

The luciferase activities of cell lysate from both bovine aorta endothelial cells (FIG. 7A) and smooth muscle cells (FIG. 7B) transfected with AWBP-PEG-g-PLL/pDNA complexes were significantly decreased with an increase of free AWBP concentrations from 31.25 μM to 500 μM. These results indicated that the existence of targeting moiety, free AWBP, could significantly inhibit gene transfer to artery cell walls by AWBP-PEG-g-PLL/pDNA complexes. In the cases of control systems such as PLL/pDNA and PEG-g-PLL/pDNA, the luciferase activities were not further decreased with the increase of free AWBP concentration by 1000 mM in both cell types (FIGS. 7A & 7B). These data demonstrated that gene transfection of AWBP-PEG-g-PLL/pDNA complexes to artery wall cells proceeded via a specific receptor-mediated pathway related to AWBP.

The invention claimed is:

1. A composition of matter comprising an artery wall binding peptide (SEQ ID NO:2) covalently coupled to a pharmaceutically acceptable cationic molecule, complex, or conjugate, wherein said cationic molecule, complex, or conjugate is configured for complexing with a nucleic acid.

2. The composition of matter of claim 1 wherein said artery wall binding peptide (SEQ ID NO:2) is present in a molar ratio to said cationic molecule, complex, or conjugate of greater than 1:1.

3. The composition of matter of claim 2 wherein said artery wall binding peptide (SEQ ID NO:2) is present in a molar ratio to said cationic molecule, complex, or conjugate of at least 2:1.

4. The composition of matter of claim 1 wherein said cationic molecule, complex, or conjugate comprises a cationic polymer.

5. The composition of matter of claim 4 wherein said cationic polymer comprises poly(L-lysine).

6. The composition of matter of claim 4 wherein said cationic polymer comprises poly(ethylene glycol)-grafted-poly(L-lysine).

7. A composition of matter having the formula (AWBP)$_n$-PEG-g-PLL, wherein AWBP is an artery wall binding peptide (SEQ ID NO: 2), n is an integer of at least 1, and PEG-g-PLL is poly(ethylene glycol)-grafted-poly(L-lysine).

8. The composition of matter of claim 7 wherein n is 4.

9. A composition of matter comprising artery wall binding peptide (SEQ ID NO:2) covalently coupled to poly(ethylene glycol)-grafted-poly(L-lysine).

10. The composition of matter of claim 9 wherein artery wall binding peptide (SEQ ID NO:2) is covalently coupled to poly(ethylene glycol)-grafted-poly(L-lysine) in a molar ratio of about 4:1.

11. A method of making a composition having the formula: (AWBP)$_n$-PEG-g-PLL, wherein AWBP is an artery wall binding peptide (SEQ ID NO: 2), n is an integer of at least 1, and PEG-g-PLL is poly(ethylene glycol)-grafted-poly(L-lysine), comprising: (a) conjugating poly(ethylene glycol) to poly(L-lysine) to result in poly(ethylene glycol)-grafted-poly(L-lysine); and (b) conjugating artery wall binding peptide (SEQ ID NO: 2) to the poly(ethylene glycol)-grafted-poly(L-lysine) to result in (AWBP)$_n$-PEG-g-PLL.

12. The method of claim 11 wherein n is 4.

13. A method for delivering a nucleic acid to a cell in vitro bearing a receptor that binds an artery wall binding peptide (SEQ ID NO: 2) comprising: (a) mixing the nucleic acid with a composition of matter comprising an artery wall binding peptide (SEQ ID NO: 2) covalently coupled to poly(ethylene glycol)-grafted-poly(L-lysine) to result in a complex comprising a nucleic acid, a poly(ethylene glycol)-grafted-poly(L-lysine) and an artery wall binding peptide (SEQ ID NO: 2) and (b) causing the complex to contact the cell in vitro such that the receptor binds the artery wall binding peptide (SEQ ID NO: 2), thereby delivering the nucleic acid to the cell.

14. The method of claim 13 wherein the artery wall binding peptide (SEQ ID NO:2) is covalently coupled to the poly(ethylene glycol)-grafted-poly(L-lysine) in a molar ratio of about 4:1.

* * * * *

SEQUENCE LISTING

<160> NUMBER OF SEQ ID NOS: 2

<210> SEQ ID NO 1
<211> LENGTH: 17
<212> TYPE: PRT
<213> ORGANISM: Homo sapiens

<400> SEQUENCE: 1

Arg Ala Leu Val Asp Thr Leu Lys Phe Val Thr Gln Ala Glu Gly Ala
1               5                   10                  15

Lys

<210> SEQ ID NO 2
<211> LENGTH: 19
<212> TYPE: PRT
<213> ORGANISM: Homo sapiens

<400> SEQUENCE: 2

Cys Gly Arg Ala Leu Val Asp Thr Leu Lys Phe Val Thr Gln Ala Glu
1               5                   10                  15

Gly Ala Lys